United States Patent [19]

Otani

[11] Patent Number: 4,921,676
[45] Date of Patent: May 1, 1990

[54] SHAKING APPARATUS FOR AGITATING AND WITHDRAWING A SPECIMEN IN A SEALED VESSEL

[75] Inventor: Masanori Otani, Kakogawashi, Japan

[73] Assignee: Toa Medical Electronics Co., Ltd., Kobe, Japan

[21] Appl. No.: 78,718

[22] Filed: Jul. 28, 1987

[30] Foreign Application Priority Data

Jan. 29, 1987 [JP] Japan ................... 62-019314

[51] Int. Cl.⁵ .................... B01L 3/02; B01F 11/00
[52] U.S. Cl. .................... 422/100; 366/111; 366/114
[58] Field of Search ........ 422/68, 73, 99, 100, 422/64, 65, 63, 103, 104, 258, 259; 73/863.44, 863.45; 366/111, 114, 140, 191, 210, 212, 213, 215, 216, 217, 342

[56] References Cited

U.S. PATENT DOCUMENTS

| | | | |
|---|---|---|---|
| 3,614,434 | 10/1971 | Horwitz et al. | 366/140 |
| 3,975,001 | 8/1976 | Moore et al. | 366/216 |
| 4,046,515 | 9/1976 | de Leeuw | 422/100 |
| 4,265,544 | 5/1981 | Banno et al. | 422/99 |
| 4,345,843 | 8/1982 | Berglund et al. | 422/99 |
| 4,415,270 | 11/1983 | Heinis et al. | 366/216 |
| 4,475,411 | 10/1984 | Wellerfors | 73/864.24 |

FOREIGN PATENT DOCUMENTS 76765  5/1983  Japan.
142752  9/1984  Japan.

Primary Examiner—Barry S. Richman
Assistant Examiner—T. J. Wallen
Attorney, Agent, or Firm—Barnes & Thornburg

[57] ABSTRACT

A shaking apparatus for agitating and withdrawing a liquid specimen such as blood confined in a sealed vessel, the apparatus including vessel catching hand whereby the vessel is held under the action of a spring and is shaked so as to effect the agitation of the content, and after agitation is finished the content is withdrawn without opening the vessel through needles stabbled through the plug thereof. The needles are cleansed so as not to spoil the specimen contained in the vessel.

7 Claims, 3 Drawing Sheets

SHAKING APPARATUS FOR AGITATING AND WITHDRAWING A SPECIMEN IN A SEALED VESSEL

BACKGROUND AND SUMMARY OF THE INVENTION

The present invention relates to a shaking apparatus for agitating a specimen such as blood contained in a sealed vessel, and withdrawing the content under suction. More particularly, the present invention relates to an apparatus for shaking one or more sealed vessels mounted thereon so as to agitate the content and withdraw it under suction without opening the vessel.

For agitating a the specimen contained in a sealed vessel and withdrawing it various apparatus and methods are known in the art and are widely used, for example:

(a) A rotary vessel is provided eccentrically of the shaft of a driving motor, and the vessel is caused to oscillate, thereby mixing the liquids contained therein. After the mixing is finished, a nozzle or needle is inserted through the plug of the vessel, thereby allowing the mixture to be withdrawn through the needle. (Japanese Utility Model Unexamined publication No. 59-142752)

(b) A specially shaped carrier like a ferriswheel is provided on which several vessels are radially arranged. By rotating the carrier, the liquids contained in the individual vessels are mixed. After the mixing is finished, a nozzle or needle is inserted through the plug of each vessel, thereby allowing the mixture to be withdrawn through the needle. (U.S. Pat. No. 4,475,411)

(c) An apparatus having no agitator but effecting the withdrawal of the content is provided. In this apparatus, the vessels are held in recesses of a cradle (rack), and a double-walled needle is inserted through the plug of each vessel so as to withdraw the liquids. (Japanese Patent Unexamined Publication No. 58-76765).

The known apparatus and methods mentioned above have the following disadvantages:

The apparatus referred to in (a) is suitable for agitating the liquids when they are in small quantities, but when in large quantities the liquid tends to be insufficiently agitated.

The ferris-wheel like carrier in (b) requires a large quantity of liquid to be withdrawn because of its relatively long path from the sampling nozzle to the analyzing unit. To withdraw the large quantity of liquid, the pressure must be accordingly large, which endangers the plug of the vessel. Another disadvantage is that only a limited number of vessels can be mounted on the carrier.

The apparatus referred to in (c) must be equipped with an extra agitator, or else the vessel must be shaken by hand to agitate the content. The rack has recesses for securing the vessels therein. The shapes of the recesses are predetermined, which means that the vessels mounted on the rack must have a shape corresponding to the particular shape of the recess. In addition, it is difficult to stab a double-walled needle in the plug of the vessel, and furthermore, the complicated structure of the apparatus leads to a high production cost.

An object of the present invention is to provide an apparatus which solves the problems pointed out with respect to the known shaking apparatus discussed above. Thus an object of the present invention is to provide a shaking apparatus capable of performing two-fold functions, specifically, the mixing of a specimen confined in a sealed vessel, and the withdrawing of the mixture under suction: The invention thereby eliminates the necessity of opening the sealed vessel.

This object is achieved by providing a shaking apparatus for agitating and withdrawing a liquid specimen in which the liquid specimen is disposed in at least one sealed vessel having a plug on one end. The apparatus includes vessel holding elements. The vessel holding elements are movable in a forward direction, in a backward direction, in an upward direction and in a backward direction. First driving elements move the vessel holding elements in the forward direction and the backward direction. Second holding elements move the vessel holding elements in the upward direction and the downward direction. Third driving elements reciprocally rotate the vessel holding elements in a predetermined angular range. Vessel tilting means are provided for tilting the vessel such that the plug faces toward the downward direction. Specimen withdrawing elements are provided which include two needles adapted to be stabbed through the plug of the vessel. One of the needles allows air to pass into the vessel and the other needle allows a liquid specimen to pass out of the vessel. A needle cleansing tank is provided for cleaning the needles. The needle cleansing tank includes apertures through which the needles are inserted for cleansing.

Other objects and advantages of the present invention will become more apparent from the following detailed description, when taken in conjunction with the accompanying drawings which show, for the purpose of illustration only, one embodiment in accordance with the present invention.

DETAILED DESCRIPTION OF THE DRAWINGS

Figure 1:
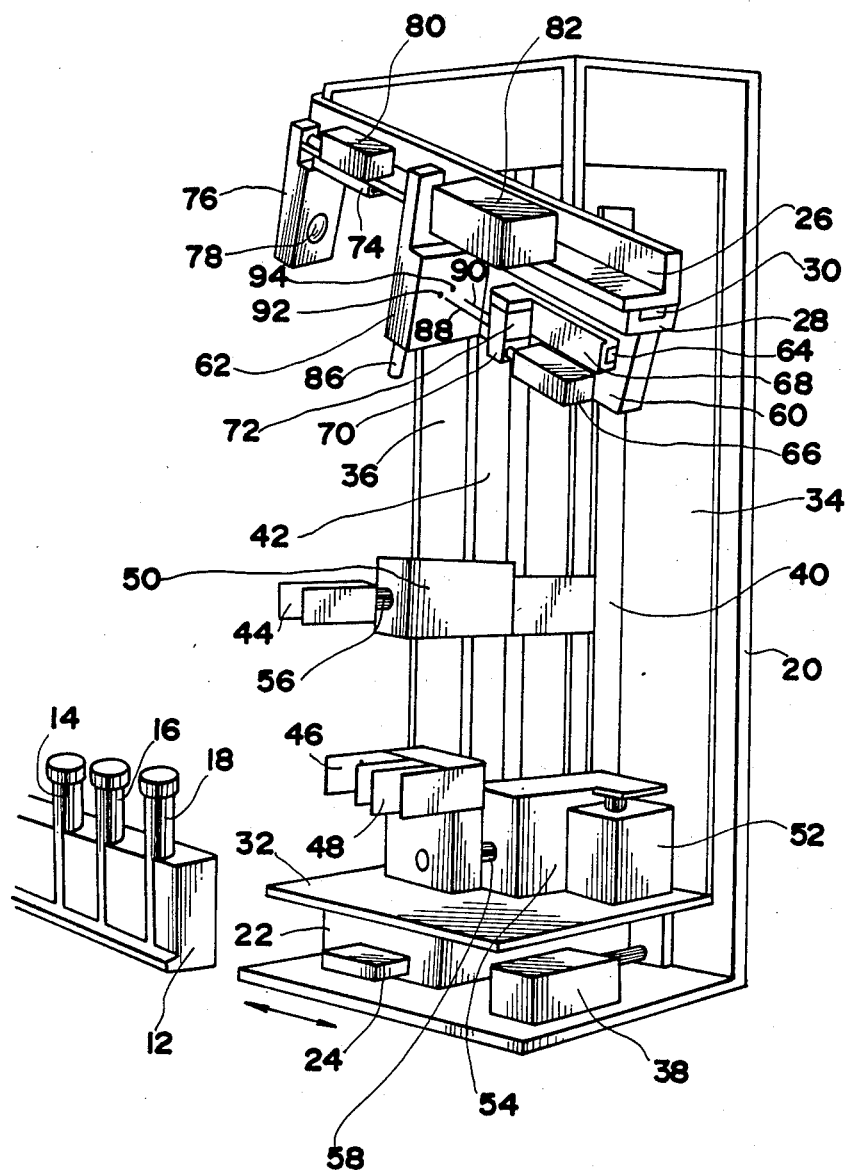
FIG. 1 is a perspective view showing a shaking apparatus according to certain embodiments of the present invention.

The shaking apparatus of the invention is generally indicated by the reference numeral 10. There is provided a rack 12 on which vessels 14, 16 and 18 are mounted. The apparatus 10 includes a supporting structure 20 which includes a guide rail 24 for a first slider 22 and a support 26. The support 26 includes a guide rail 30 for a second slider 28.

The first slider 22 is provided with a base plate 32 on which a first wall 34 and a second wall 36 are erected. The base plate 32 and the two walls 34, 36 are moved as a unit along the guide rail 24 by means of a pneumatic cylinder 38. The first wall 34 is provided with a pneumatic cylinder 40, and the second wall 36 is provided with a guide rail 42, the cylinder 40 and second wall 36 being upright. The cylinder 40 is not a piston type but a rodless type.

There are holding vessel catching hands (holding elements) 44, 46 and 48, hereinafter referred to merely as hands, which are initially situated as high as the vessels 14, 16 and 18 mounted on the rack 12. As the rack 12 moves, the vessels 14, 16 and 18 are caused to come near the hands 44, 46 and 48. Then the movement of the rack 12 is stopped. At this stage, the base plate 32 is moved forward by the cylinder 38, thereby enabling the hands 44, 46 and 48 to catch the vessels 14, 16 and 18, respectively.

Figure 3:
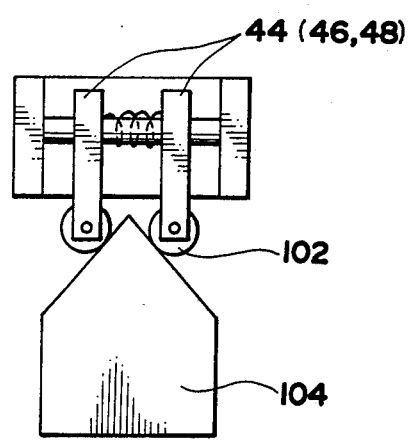
FIG. 3 is a front view of the hands.

As clearly shown in FIG. 3, each hand 44, 46 and 48 has two finger members (not numbered), each finger member having a roller bearing 102. FIG. 3 shows a state in which the roller bearings 102 come into contact with an abutment 104, thereby forcing the finger members to expand outward. In this state none of the hands catch the vessels 14, 16 and 18.

Figure 4:
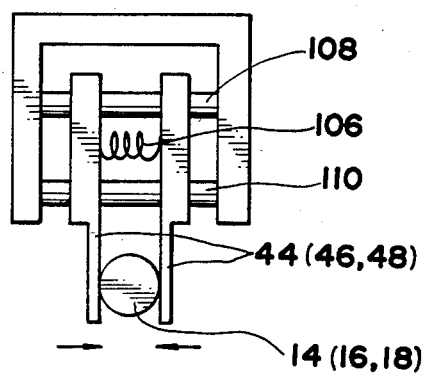
FIG. 4 is a plan view of the hands.

The cylinder 40 is then operated to raise the hand 44 along the guide rail 42, and the cylinder 52 is operated to raise the hands 46 and 48 along it, thereby separating the roller bearings 102 from the abutment 104. The finger members are drawn toward each other by a spring 106 as shown in FIG. 4, thereby enabling each hand 44, 46 and 48 to catch the respective vessels 14, 16 and 18 while they are ascending.

Figure 2:
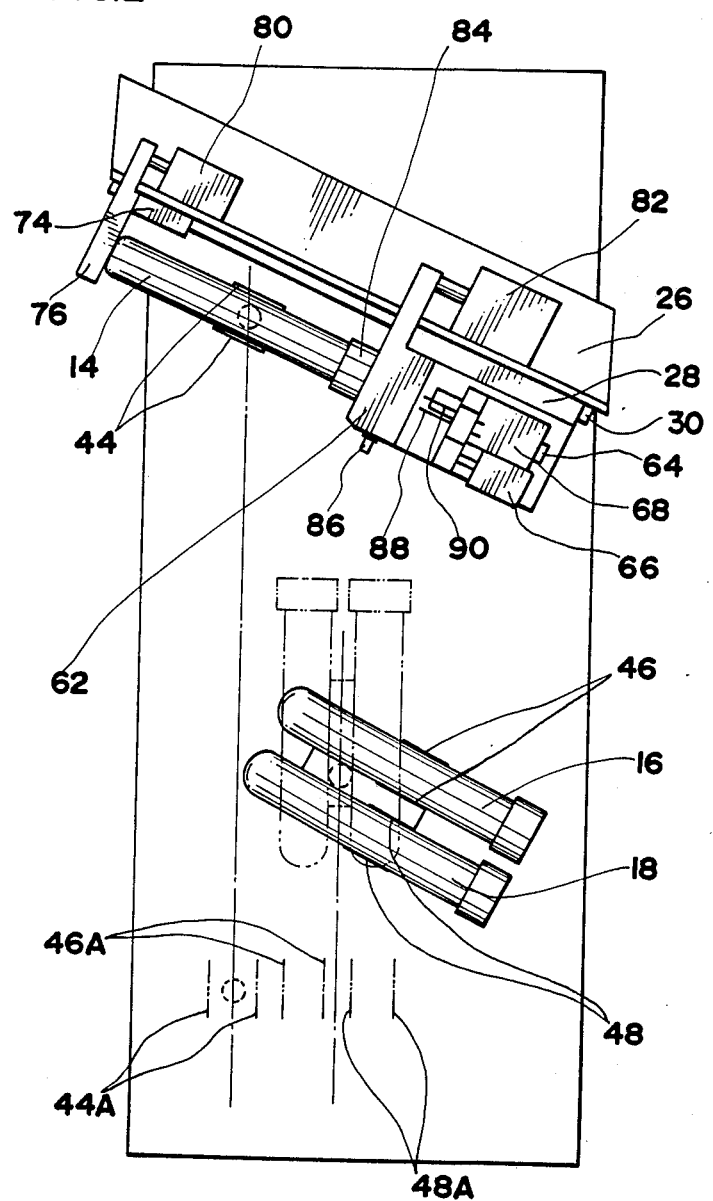
FIG. 2 is a schematic view particularly showing the movement of the vessel and the hands.

When the hand 44 ascends as high as shown in FIG. 2, it is rotated by a cylinder 50 in a 120° angular range in a plane perpendicular to the axis of the cylinder 50.

The hands 46 and 48 holding the vessels 16 and 18 are caused to ascend along the guide rail 42 virtually one-third of the height of the hand 44 shown in FIG. 2, and are then shaken in the 120° angular range in a plane perpendicular to the axis of the cylinder 54 by means of the cylinder 54. They are repeatedly shaken so as to effect the mixing of the fluids in the vessels 16 and 18. The cylinders 50 and 54 each have rotary shafts 56 and 58 linked to pinions driven by rack gears reciprocally movable, and also have sliders (not shown) movable along the guide rail 42.

The slider 28 is provided with a base plate 60 and a needle cleansing tank 62 in which a sucking needle is cleansed. The base plate 60 is provided with a pneumatic cylinder 66 and a guide rail 64, on which the slider 68 having a needle block support 70 is placed. The needle block support 70 supports a needle block 72.

A slider 74 is placed on the guide rail 30, and the slider 74 has a vessel supporter 76 with a spherical recess 78 adapted to receive the bottom of the vessel 14, 16 or 18 therein.

When the vessel 14 is situated at the position shown in FIG. 2, the cylinders 80 and 82 are operated in order to move the vessel supporter 76 and the needle cleansing tank 62, thereby holding the vessel 14 therebetween. Since the vessel supporter 76 supports the vessel 14 in its tilted posture with the plug 84 downward, the specimen therein tends to gather around the plug 84.

The needle cleansing tank 62 is provided with an outlet 86 in its bottom, through which a used cleansing agent is discharged. The tank 62 includes two apertures 92 and 94 through which needles 88 and 90 are inserted.

When the vessel 14 is held at the position and in the posture shown in FIG. 2, the cylinder 66 is operated to cause the sliders 68 to move toward the vessel 14, thereby enabling the needles 88 and 90 to stab the plug 84 through the apertures 92 and 94 until the tips of the needles reach the liquid in the vessel 14. At this stage the movement of the needles is stopped, and air is supplied into the vessel 14 through one of the needles 88 or 90, and the liquid is withdrawn through the other needle 90 or 88.

The needle cleansing tank 62, as its name implies, is to cleanse the needles 88 and 90. After the needles 88 and 90 are inserted into the tank 62, a cleansing agent is supplied not only through a mouthpiece (not shown) located in an upper section of the tank but also through the needles 88 and 90 themselves. In this way the insides of the needles 88 and 90 are cleansed. The used cleaning agent is discharged through the outlet 86.

A typical example of operation will be described:

When the hands 44, 46 and 48 are at the positions 44A, 46A and 48A shown in FIG. 2, and when the rack 12 is moved to enable one vessel placed thereon to come to the position 48A, the hand 48 is caused to move forward and catch the vessel under the action of the spring 106. Then the hand 44 ascends up to the position shown in FIG. 2, and the hands 46, 48 repeat reciprocal rotary movements in the 120° angular range in a plane perpendicular to the cylinder 54, thereby agitating the liquid confined in the sealed vessel. During the agitation in this vessel, the liquid in the other vessel caught by the hand 44 is withdrawn under suction. After the liquid in each vessel is withdrawn, the hands 44, 46 and 48 return to in front of their original positions 44A, 46A and 48A, where the respective roller bearings 102 come into engagement with the abutments 104. Thus the vessels are released from the hands, and returned to the rack 12. After the hands 44, 46 and 48 retreat backward, the rack 12 is moved one step leftward. Thus the first-mentioned vessel comes to the position 46A, and is caught by the hand 46, whereby the same procedure is repeated. The liquid therein is again agitated. The rack 12 is moved a further step leftward, thereby enabling this vessel to come to the position 44A where it is caught by the hand 44 and held at the same position as that of the vessel 14 in FIG. 2. At this position the liquid therein is withdrawn under suction.

In the illustrated embodiment one vessel is shaken twice by the hands 46 and 48 for agitation, and is subjected to suction for withdrawal when it is caught by the hand 44. However it is possible to effect the agitation and withdrawal by one hand.

According to the present invention the following advantages result:

(1) The vessel is repeatedly shaken, thereby ensuring that the liquid therein is fully agitated irrespective of any quantity.

(2) The vessel is securely held by the hand under the action of the spring irrespective of any diameters thereof.

(3) The liquid in the sealed vessel is withdrawn under suction through a needle stabbed through the plug of the vessel, wherein there is no need for a special type of needle and an ordinary needle suffices.

(4) Several vessels can be mounted on a single rack, and by sending several racks consecutively, a large quantity of specimen can be dealt with for analysis without discontinuing the operation.

(5) The apparatus can be located near or within the analyzing unit, and the flowing paths from the apparatus to the analyzing unit can be shortened. The shortened path is advantageous in that the amount of specimen to be withdrawn can be minimized and that the pressure to be used can also be reduced. This avoids the risk of breaking the vessel.

Although the present invention has been described and illustrated in detail, it is to be clearly understood that the same is by way of illustration and example only, and is not to be taken by way of limitation. The spirit and scope of the present invention are to be limited only by the terms of the appended claims.

What is claimed is:

1. A shaking apparatus for agitating and withdrawing a liquid specimen in at least one sealed vessel having a plug on one end, said apparatus comprising:
   a frame means having upper and lower ends;
   vessel holding means supported by said frame means and displaceable between said upper and lower ends of said frame means for holding at least one vessel by spring means, said vessel holding means being movable in a forward direction, in a backward direction substantially opposite to said forward direction, in an upward direction substantially transverse to said forward and backward directions and in a downward direction substantially opposite to said upward direction;
   first driving means supported by said frame means for moving said vessel holding means in said forward direction and in said backward direction;
   second driving means supported by said frame means for moving said vessel holding means in said upward direction and in said downward direction;
   third driving means supported by said frame means for reciprocally rotating said vessel holding means in a predetermined angular range;
   tilting means supported by said frame means in an area of said upper end of said frame means for tilting said vessel holding means such that a vessel plug accommodating end thereof faces toward said downward direction;
   specimen withdrawing means supported by said frame means adjacent said tilting means and including two needles adapted to be stabbed through a plug of a vessel held in the vessel holding means, one of said needles allowing air to pass into said vessel and the other needle allowing said liquid specimen to pass out of said vessel; and
   a needle cleansing tank for cleaning the needles, said needle cleansing tank including apertures therein through which said needles are inserted for cleansing, said needle cleansing means being positioned between the specimen withdrawing means and the tilting means.

2. An apparatus as in claim 1, wherein the predetermined angular range is a 120° range.

3. An apparatus as in claim 1, wherein said first driving means includes:
   a guide rail;
   a slider moveably and slidingly disposed on said guide rail;
   a base plate disposed on said slider; and
   a cylinder means for moving said slider and said base plate on said guide rail.

4. An apparatus as in claim 1, wherein said second driving means includes:
   a first wall and a second wall;
   a guide rail disposed on said second wall; and
   a cylinder means disposed on said first wall for moving said vessel holding means in said upward and said downward directions along said guide rail.

5. An apparatus as in claim 1, wherein said third driving means include a first rotating cylinder and a second rotating cylinder, each of said rotating cylinders including a rotary shaft disposed therein, said rotary shafts being attached to said vessel holding means, said rotating cylinders and said rotary shafts providing the rotation of said vessel holding means.

6. An apparatus as in claim 1, wherein said tilting means includes:
   a support;
   a first slider disposed on a guide rail;
   a second slider;
   a vessel supporter having a spherical recess adapted to secure the vessel therein and being disposed on said first slider; and
   a cylinder means associated with said support and said vessel supporter for moving said support and said vessel supporter towards and away from one another.

7. An apparatus as in claim 1, wherein said specimen withdrawing means comprises:
   a base plate;
   a guide rail disposed on said base plate;
   a slider slidingly disposed on said guide rail;
   a needle block support disposed on said slider;
   a needle block including said two needles disposed thereon supported on said needle block support; and
   a cylinder means disposed on said base plate for moving said slider toward and away from said plug of said vessel.

* * * * *